United States Patent [19]

Vallee et al.

[11] Patent Number: 4,897,464

[45] Date of Patent: Jan. 30, 1990

[54] PURIFIED PROTEIN HAVING ANGIOGENIC ACTIVITY AND METHODS OF PREPARATION

[75] Inventors: Bert L. Vallee, Brookline; James W. Fett, Waltham, both of Mass.

[73] Assignee: President and Fellows of Harvard College, Cambridge, Mass.

[21] Appl. No.: 63,252

[22] Filed: Jun. 25, 1987

Related U.S. Application Data

[63] Continuation of Ser. No. 778,387, Sep. 20, 1985, Pat. No. 4,727,137, Continuation-in-part of Ser. No. 724,088, Apr. 17, 1985, abandoned.

[51] Int. Cl.⁴ .................... C07K 13/00; A61K 37/00
[52] U.S. Cl. .................... 530/350; 530/399; 530/827; 530/828; 435/70.3; 514/2; 514/8; 514/12; 514/21
[58] Field of Search ............... 530/350, 399, 827–828; 435/68, 70; 574/21, 2, 8, 12

[56] References Cited

U.S. PATENT DOCUMENTS

| | | |
|---|---|---|
| 4,229,521 | 10/1980 | Tolbert et al. .................. 435/68 |
| 4,268,629 | 5/1981 | Tolbert et al. .................. 435/240 |
| 4,503,038 | 3/1985 | Banda .................. 514/21 |
| 4,529,590 | 7/1985 | LeVeen et al. .................. 424/85 |
| 4,568,640 | 2/1986 | Rubin .................. 435/68 |
| 4,698,301 | 10/1987 | Weiss et al. .................. 435/240.25 |
| 4,699,788 | 10/1987 | Catsimpoalas et al. .................. 424/95 |

OTHER PUBLICATIONS

Vallee et al, *Experientia*, 41(1), 1985, pp. 1–15.
Burgas, CA, vol. 106(9), 1986, #61814x.
Weiss et al, CA, vol. 102(3), #18338a, 1984.
Mascatelli et al, CA, vol. 104(23), #200508z, 1986.
Folkman et al., *J. Exp. Med.*, vol. 133, 1971, pp. 275–288.

*Primary Examiner*—Garnette D. Draper
*Attorney, Agent, or Firm*—Allegretti & Witcoff, Ltd.

[57] ABSTRACT

A substantially pure protein having angiogenic activity is disclosed. A method for preparing proteins having angiogenic activity from cell culture media is also disclosed. Proteins produced according to the invention are useful in the diagnosis of malignancies, for promoting wound healing, and for other diagnositc and therapeutic purposes.

2 Claims, 2 Drawing Sheets

Fig. 2

```
  1                                                                    15
<Glu-Asp-Asn-Ser-Arg-Tyr-Thr-His-Phe-Leu-Thr-Gln-His-Tyr-Asp-
                                                                       30
Ala-Lys-Pro-Gln-Gly-Arg-Asp-Asp-Arg-Tyr-Cys-Glu-Ser-Ile-Met-
                                                                       45
Arg-Arg-Arg-Gly-Leu-Thr-Ser-Pro-Cys-Lys-Asp-Ile-Asn-Thr-Phe-
                                                                       60
Ile-His-Gly-Asn-Lys-Arg-Ser-Ile-Lys-Ala-Ile-Cys-Glu-Asn-Lys-
                                                                       75
Asn-Gly-Asn-Pro-His-Arg-Glu-Asn-Leu-Arg-Ile-Ser-Lys-Ser-Ser-
                                                                       90
Phe-Gln-Val-Thr-Thr-Cys-Lys-Leu-His-Gly-Gly-Ser-Pro-Trp-Pro-
                                                                      105
Pro-Cys-Gln-Tyr-Arg-Ala-Thr-Ala-Gly-Phe-Arg-Asn-Val-Val-Val-
                                                                      120
Ala-Cys-Glu-Asn-Gly-Leu-Pro-Val-His-Leu-Asp-Gln-Ser-Ile-Phe-
         123
Arg-Arg-Pro-OH.
```

PURIFIED PROTEIN HAVING ANGIOGENIC ACTIVITY AND METHODS OF PREPARATION

This application is a continuation of application Ser. No. 778,387, filed Sept. 20, 1985, now U.S. Pat. No. 4,727,137, and a continuation-in-part of our co-pending application U.S. Ser. No. 724,088, filed Apr. 17, 1985, now abandoned which are hereby incorporated by reference.

FIELD OF THE INVENTION

The present invention relates to angiogenesis factors and their preparation. More specifically, the present invention relates to a novel angiogenic protein and its preparation from cell culture media.

BACKGROUND ART

Angiogenesis, the process of developing a hemovascular network, is essential for the growth of solid tumors and is a component of the normal wound healing and growth processes. It has also been implicated in the pathophysiology of atherogenesis, arthritis, and diabetic retinopathy. It is characterized by the directed growth of new capillaries toward a specific stimulus. This growth, mediated by the migration of endothelial cells, may proceed independently of endothelial cell mitosis.

The molecular messengers responsible for the process of angiogenesis have long been sought. Greenblatt and Shubik (*J. Natl. Cancer Inst.* 41: 111–124, 1968) concluded that tumor-induced neovascularization is mediated by a diffusible substance. Subsequently, a variety of soluble mediators have been implicated in the induction of neovascularization. These include prostaglandins (Auerbach, in *Lymphokines,* Pick and Landy, eds., 69–88, Academic Press, New York, 1981), human urokinase (Berman et al., *Invest Opthalm. Vis. Sci.* 22: 191–199, 1982), copper (Raju et al., *J. Natl. Cancer Inst.* 69: 1183–1188, 1982), and various "angiogenesis factors".

Angiogenesis factors have been derived from tumor cells, wound fluid (Banda et al., *Proc. Natl. Acad. Sci USA* 79: 7773–7777, 1982; Banda et al., U.S. Pat. No. 4,503,038), and retinal cells (D'Amore, *Proc. Natl. Acad. Sci. USA* 78: 3068–3072, 1981). Tumor-derived angiogenesis factors have in general been poorly characterized. Folkman et al. (*J. Exp. Med.* 133: 275–288, 1971) isolated a tumor angiogenesis factor from the Walker 256 rat ascites tumor. The factor was mitogenic for capillary endothelial cells and was inactivated by RNase. Tuan et al. (*Biochemistry* 12: 3159–3165, 1973) found mitogenic and angiogenic activity in the nonhistone proteins of the Walker 256 tumor. The active fraction was a mixture of proteins and carbohydrate. A variety of animal and human tumors have been shown to produce angiogenesis factor(s) (Phillips and Kumar, *Int. J. Cancer* 23: 82–88, 1979) but the chemical nature of the factor(s) was not determined. A low molecular weight non-protein component from Walker 256 tumors has also been shown to be angiogenic and mitogenic (Weiss et al., *Br. J. Cancer* 40: 493–496, 1979). An angiogenesis factor with a molecular weight of 400–800 daltons was purified to homogeneity by Fenselau et al. (*J. Biol. Chem.* 256: 9605–9611, 1981), but it was not further characterized. Human lung tumor cells have been shown to secrete an angiogenesis factor comprising a high molecular weight carrier and a low molecular weight, possibly non-protein, active component (Kumar et al., *Int. J. Cancer* 32: 461–464, 1983). Vallee et al (*Experientia.* 41: 1–15, 1985) found angiogenic activity associated with three fractions from Walker 256 tumors. Tolbert et al. (U.S. Pat. No. 4,229,531) disclose the production of angiogenesis factor from the human adenocarcinoma cell line HT-29, but the material was only partially purified and was not chemically characterized.

Isolation of angiogenesis factors has employed high performance liquid chromatography (Banda et al., ibid); solvent extraction (Folkman et al., ibid); chromatography on silica gel (Fenselau et al., ibid), DEAE cellulose (Weiss et al., ibid), or Sephadex (Tuan et al., ibid); and affinity chromatography (Weiss et al., ibid).

Because angiogenesis factors play an important role in wound healing (Rettura et al., FASEB abstract #4309, 61st annual meeting, Chicago, 1977) and may find applicability in the development of screening tests for malignancies (Klagsburn et al., *Cancer Res.* 36: 110–114, 1976; and Brem et al., *Science* 195: 880–881, 1977), it would clearly be advantageous to obtain a homogeneous preparation of a well characterized angiogenesis factor.

DISCLOSURE OF THE INVENTION

Briefly stated, the present invention discloses substantially pure proteins of human origin having angiogenic activity. A substantially pure protein having angiogenic activity and characterized by a molecular weight between 12,500 daltons and 17,500 daltons (preferably between 14,000 and 15,000 daltons) and an isoelectric point greater than 9.5 is also disclosed. In a preferred embodiment, the protein is derived from human adenocarcinoma HT-29 cells and is further chracterized by a molecular weight of approximately 14,193 daltons as determined by amino acid sequence analysis and a lack of mitogenic activity toward 3T3 cells as determined by conventional assay procedures.

A related aspect of the present invention discloses a therapeutic composition comprising a substantially pure protein having angiogenic activity and characterized by a molecular weight between 12,500 daltons and 17,500 daltons (preferably between 14,000 and 15,000 daltons) and an isoelectric point greater than 9.5, and a pharmaceutically acceptable carrier.

An additional aspect of the present invention discloses a diagnostic composition comprising a substantially pure protein having angiogenic activity and characterized by a molecular weight between 12,500 daltons and 17,500 daltons and an isoelectric point greater than 9.5.

A further aspect of the invention discloses a process for obtaining a substantially pure protein having angiogenic activity from a conditioned cell culture medium. The process comprises (a) treating the medium to remove high molecular weight proteins; (b) binding a portion of the treated medium to a cation exchange matrix; (c) eluting the bound portion from the matrix to produce an eluate; (d) fractionating the eluate by high performance liquid chromatography; and (e) collecting the fraction containing the protein.

Other aspects of the invention will become evident upon reference to the detailed description and attached drawings.

BRIEF DESCRIPTION OF THE DRAWINGS

FIG. 2 illustrates the amino acid sequence of angiogenin.

BEST MODE FOR CARRYING OUT THE INVENTION

Figure 1:
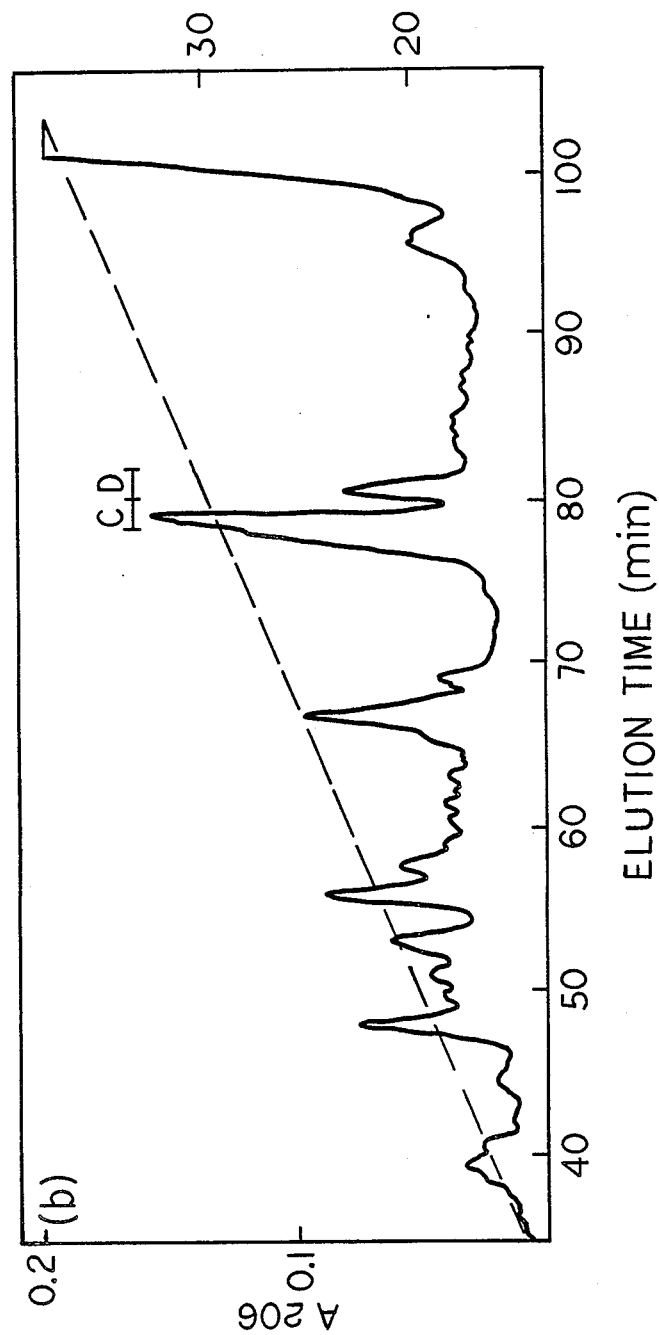
FIG. 1 illustrates a high performance liquid chromatography profile of material eluted from a carboxymethyl cellulose column. The eluted material was fractionated by reversed phase high performance liquid chromatography using a gradient of isopropanol/acetonitrile/water (5:5:4 v/v/v) containing 0.08% TFA. Fractions C and D were active in angiogenesis assays.

Prior to setting forth the invention, it may be helpful to define certain terms to be used hereinafter.

Angiogenic activity is the chemical stimulation of hemovascular development in tissue. It is generally associated with diffusible substances produced by a variety of cell types. Angiogenic activity may be characterized by a positive response in the chick embryo chorioallantoic membrane assay (Knighton et al., *Br. J. Cancer* 35: 347-356, 1977; the disclosure of which is incorporated herein by reference in its entirety) and/or the rabbit cornea implant assay (Langer and Folkman, *Nature* 263: 797-800, 1976; the disclosure of which is incorporated herein by reference in its entirety).

Mitogenic activity is the chemical stimulation of cell division. This activity is characterized by the stimulation of $^3$H-thymidine incorporation into 3T3 cells (Klagsburn et al., *Exp. Cell Res.* 105: 99-108, 1977; the disclosure of which is incorporated herein by reference in its entirety).

Ribonuclease activity is characterized by the degradation of large RNA molecules, such as the 28S and 18S ribosomal RNAs, to lower molecular weight species.

As discussed above, angiogenesis factors have been derived from a variety of sources, but have not heretofore been purified to homogeneity and characterized as to chemical composition and physical properties. Through the use of a novel multistep process described herein, it was discovered that tumor cells produce a protein of molecular weight approximately 12,500 to 17,500 daltons and an isoelectric point greater than 9.5 which has angiogenic activity. The angiogenic material obtained by this process consists essentially of a single homogeneous protein component as determined by conventional assay methods, which is suitable for use in therapeutic and diagnostic compositions.

Tumor cells are the preferred source of an angiogenic protein of the present invention, although normal cells, for example retinal cells, are known to produce angiogenesis factors. A particularly preferred cell line is the human adenocarcinoma cell line HT-29 (Fogh and Trempe, in *Human Tumor Cells In Vitro*, Fogh, ed., 115-160, Plenum, New York, 1975). Specifically, isolates of that cell line are deposited as ATCC HTB38 and as ATCC CRL8905. The cells may be cultured according to known methods, e.g., as monolayer cultures in Dulbecco's modified Eagle's medium or other suitable media. A preferred medium is Dulbecco's modified Eagle's medium supplemented with 2 mM L-glutamine and 5% heat inactivated fetal bovine serum (DME/5). The medium is changed periodically and cells are subcultured according to known procedures.

To facilitate isolation of angiogenic protein(s) from the cell medium, it is preferred that the cells be transferred to a serum free maintenance medium once they have reached confluent growth. A preferred maintanance medium is DME/5 without serum but containing L-glutamine at a concentration of 5 mM .

Medium in which cells have been cultured or maintained, known as conditioned medium, is then removed from the cells and preferably filtered to remove cell debris, then treated to remove high molecular weight (generally greater than 50,000 daltons) proteins. A preferred method of treatment is acidification, e.g. by the addition of glacial acetic acid to a concentration of 5% (v/v), followed by centrifugation. It may also be desirable to concentrate the filtered, acidified medium prior to further purification steps.

The filtered, treated medium is then chromatographed on a cation exchange matrix. A preferred such cation exchange matrix is carboxymethyl cellulose (CM cellulose). It is preferred that the acidified, conditioned medium be lyophilized, reconstituted in 0.1M sodium phosphate buffer pH 6.6, and applied to the matrix. Under such conditions, the angiogenesis factor(s) will bind to the matrix and is eluted preferably with the same buffer containing 1M NaCl.

The eluate from the cation exchange matrix is further fractionated by reversed-phase high performance liquid chromatography. The eluate is lyophilized, reconstituted in a suitable solvent, such as 0.1% trifluoroacetic acid (TFA) in water, and eluted by applying a gradient of a second solvent to the column. A linear gradient of isopropanol/acetonitrile/water (5:5:4 v/v/v) containing 0.08% TFA is preferred. Material eluted from the HPLC column may then be dialyzed to remove the solvent, lyophilized, and reconstituted.

In a preferred embodiment, the lyophilized eluate from the cation exchange matrix is reconstituted in a suitable solvent, such as 0.01M Tris pH 8.0, and applied to a cation exchange HPLC colum. Bound material is then eluted from the column, e.g., by applying a linear gradient of NaCl in 0.01M Tris pH 8.0, to produce a second eluate. The second eluate is then fractionated by reversed-phase HPLC as described above.

In an additional preferred embodiment, the reconstituted HPLC column eluate is further purified by a second cation exchange chromatography step. A preferred chromatography matrix is CM cellulose, used under conditions described above. The material eluted from the matrix is lyophilized and reconstituted in water.

The reconstituted eluate from the HPLC column, or from the second cation exchange chromatography step, is then assayed for biological, activity to identify the active fraction(s). Several assays for angiogenic activity are well known in the art, including the chick embryo chorioallantoic membrane assay (Knighton et al., *Br. J. Cancer* 35: 347-356, 1977) and the cornea implant assay (Langer and Folkman, *Nature* 263: 797-800, 1976).

When HT-29 cells are employed as the starting material, two active fractions were obtained from the HPLC column. One fraction contains a major protein component of $M_r$ approximately 16,000 and lesser amounts of a $M_r$ approximately 14,000 species. The second fraction contains a single protein species of $M_r$ approximately 14,000, which has been designated angiogenin. On further analysis, angiogenin was found to have an isoelectric point greater than 9.5 and a molecular weight of approximately 14,193 daltons by amino acid sequence analysis. Surprisingly, in contrast to most previously described angiogenesis factors, angiogenin is not mitogenic in conventional assays. The amino acid sequence of angiogenin was also determined and it was found to be 35% homologous to the pancreatic ribonucleases. Angiogenin was further shown to possess highly specific ribonuclease activity.

It will be appreciated that other forms of angiogenin may exist due to genetic polymorphism or through in vivo modifications of the protein itself or of precursors thereof. Additionally, angiogenic proteins according to the present invention may be modified by in vitro methods and still retain angiogenic activity (Vallee et al., ibid). For example, based on the homology with ribonuclease, the disulphide bonds (Cys-26 to Cys-81, Cys-39 to Cys-92, Cys-57 to Cys-107), the histidines at positions 13 and 114, and the lysine at position 40 of angiogenin may be chemically modified either singly or in combination to alter the biological activity of the molecule. An increase in the biological activity could permit the use of lower dosage levels. A molecule having reduced angiogenic activity or no angiogenic activity, but retaining certain structural features, could still bind receptors on endothelial or other cells and, by blocking the site of action, form an antagonist to the action of natural angiogenin, resulting in an approach to the treatment of angiogenesis-related disease states. Such modified forms of angiogenin are within the scope of the present invention. Specifically, within the scope of the invention are proteins having little or no angiogenic activity, but which retain substantially all of the sequence shown in FIG. 2, but for modifications to one or more of: Cys-26; Cys-39; Cys-57; Cys-81; Cys-92; Cys-107; His-13; His-114; or Lys-40.

Angiogenic proteins produced according to the present invention may be used to produce therapeutic or diagnostic compositions by combining them with suitable carriers. The therapeutic compositions may be used; to promote the development of a hemovascular network in a mammal, for example, to induce collateral circulation following a heart attack, or to promote would healing, for example in joints or other locations. Preferably, the therapeutic compositions according to the present invention will be administered intravenously or by direct topical application to the wound site. For example, if injury occurs to the meniscus of the knee or shoulder as frequently occurs in sports-related injuries or osteoarthritis, injection of angiogenic proteins at the site of the injury may promote healing of torn or traumatized fibrocartilage material. Effective doses will vary according to the severity of the condition and the target tissue. Furthermore, angiogenic proteins have diagnostic applications in screening for the presence of malignancies, either by using the protein to assay for the presence of antibodies or to produce antibodies for use as immunodiagnostic reagents. A diagnostic composition containing the protein may be incubated with a biological sample under conditions suitable for the formation of an antigen-antibody complex. The formation of the complex (i.e., the presence of antibodies in the sample) is then detected. Techniques for such assays are well known in the art, e.g. the enzyme linked immunosorbent assay (Voller et al., *The Enzyme Linked Immunosorbent Assay*, Dynatech Laboratories, Inc., 1979) or the Western blot assay (see, for example, Towbin et al., *Proc. Natl Acad. Sci. USA* 76: 4350, 1979). Similarly, a diagnostic composition comprising an antibody against an angiogenic protein may be used to assay for the presence of the protein in a biological sample. The angiogenic proteins may also be used to develop angiogenesis inhibitors which may be useful in the treatment of disorders associated with angiogenesis.

EXPERIMENTAL

The following examples are offered by way of illustration and not of limitation.

Materials and Methods

CM-cellulose (grade CM-52) was a product of Whatman Ltd. All dialyses were performed with 6000–8000 molecular weight cutoff tubing (Spectra/Por). Deionized, sterile water was provided by a Milli RO-20 reverse osmosis/Milli Q water purification system (Millipore Corp., Bedford, MA). HPLC grade water was obtained from J. T. Baker Chemical Co. Pepstatin A and hen egg white lysozyme were from Sigma Chemical Co. (St. Louis, MO). Acetonitrile (J. T. Baker Chemical Co.) and isopropanol (Millipore, Waters Associates) were of HPLC grade.

Sequencer reagents were obtained from Beckman Instruments, Inc. and sequencer solvents from Burdick and Jackson Laboratories, Inc., Muskegon, MI.

Glassware used for handling protein solutions was always siliconized by treatment with dichlorodimethylsilane (Sigma Chemical Co.).

Angiogenesis was routinely assessed using the chick embryo chorioallantoic membrane (CAM) method of Knighton et al. ibid., with modifications as described previously (Vallee et al., *Experientia.* 41: 1–15, 1985). Negative or positive [i.e., the appearance of the typical "spokewheel" pattern (Folkman, *Cancer Res.* 34: 2109–2113, 1974)] responses were microscopically assessed after 1, 2 and 3 days and recorded as the number of positive angiogenic responses per number of eggs surviving per sample dilution. Statistical analysis was performed on the day 2 data. Since the only designations are as positive or negative, the assays constitute Bernoulli trials and can be analyzed as binomial distributions (Kendall and Stuart, in *The Advanced Theory of Statistics,* Vol. I, 3rd ed., p. 120, Hafner, New York, 1969). The frequency of positive responses in a series of 1,834 controls is 0.0676 (124 positive and 1,710 negative), with a standard deviation of 0.0059 (Kendall and Stuart, in *The Advanced Theory of Statistics,* Vol II, 3rd ed, Hafner, New York, 1973), yielding upper and lower 0.1% confidence limits of 0.0857 and 0.0495. Unless indicated otherwise, 0.0857, the upper limit, has been employed as the probability of obtaining a positive result with a test group of N eggs. While this decision increases the chance that the sample is classed as inactive when it is in fact active, it decreases the chance of an inactive sample being considered active. Tables of the cumulative probabilities of positive results for N=2 to N=30 were prepared using 0.0857 as the probability of a positive result, and test results are interpreted in terms of these tables. For values of N greater than 30, the cumulative distribution was evaluated using the Incomplete Beta function (Kendall and Stuart, 1969 ibid). Analogue dose-response curves were constructed by plotting the resultant probabilities against the weight of sample applied per egg. However, such plots cannot be interpreted in quantitative terms (i.e., that a 50% response can result from a defined dose), but rather as yielding the range over which and the lower limit at which a positive response is significant. A significance level of $\leq 5\%$ has to be attained for a sample to be considered active. Since the cumulative probabilities refer to discrete events they are themselves discrete, and therefore only inequalities may be specified in general.

Angiogenic activity also in the rabbit cornea using a modification of established procedures (Langer and Folkman, ibid.) that employed methycellulose instead of Elvax pellets as the implant. Stereomicroscopic observations were made every 5 days to detect infiltrating vessels extending from the corneal limbus toward the sample implant.

Cation-exchange HPLC employed a Synchropak CM 300 column (250×4.1 mm; Synchrom, Inc.) equilibrated with 20 mM sodium phosphate, pH 7.0, at a flow rate of 0.8 mL/min. Elutions were performed using a linear gradient of NaCl in the above buffer. Standards used were ribonuclease A (pI=9.5), cytochrome c (pI=10.2) and lysozyme (pI=10.5).

Analytical isoelectric focusing was carried out on an LKB 2117 multiphor unit using preformed plates (PAG plates, pH range 3.5–9.5; LKB). Gels were stained with Coomassie blue according to the manufacturer's recommendations. Standards used were ribonuclease A, cytochrome c, and lysozyme.

Protein concentrations were determined by the dye binding method of Bradford (*Anal. Biochem.* 72: 248–254, 1976) using bovine serum albumin (BSA) as standard.

Gel-filtration HPLC was performed on an LKB Ultropac TSK-G3000SW column (300×7.5 mm) equilibrated with PBS containing 6M guanidine hydrochloride at a flow rate of 0.5 mL/min. Column effluents were monitored at 206 nm. BSA ($M_r=25,000$), lysozyme ($M_r=14,400$), and insulin ($M_r=6,000$) were used as standards.

Example 1: Purification of Angiogenin

Cells from the human colorectal adenocarcinoma line HT-29 (Fogh & Trempe, ibid) were routinely grown at 37° C. as monolayer cultures in T-Flasks (Costar, Cambridge, MA) utilizing Dulbecco's modified Eagle's medium (M.A. Bioproducts, Walkersville, MD) containing 4.5 g/L glucose, 50 mg/L gentamycin, and 500 g/L fungizone (DME) supplemented with 2 mM L-glutamine and 5% heat inactivated fetal bovine serum (FBS) (DME/5) in a humidified, 7.5% $CO_2$ (in air) atmosphere. Medium was changed every 2–3 days, and cells were subcultured using standard trypsinization procedures.

$1 \times 10^8$ cells from the DME/5 culture were then inoculated into a cell factory (Vanguard International, Inc., Neptune, NJ) containing 1.5 L of DME/5 and allowed to attach and proliferate in a humidified, 7.5% $CO_2$ in air environment at 37° C. until confluent. The DME/5 was then replaced by 1.5 L of a serum-free maintenance medium consisting of DME without FBS but with an L-glutamine concentration of 5 mM. This maintenance medium was changed at 2–3 day intervals and all collections made after day 7 were processed as described below.

Cell debris was removed from the serum-free conditioned medium by sequential passage through Whatman 40 filter paper and Whatman 934-AH glass microfiber filters. Glacial acetic acid was added to the filtrate to a concentration of 5% (v/v). The acidified serum-free conditioned medium was treated with pepstatin A (5 mg/L), frozen, stored at −20° C., then thawed and clarified by filtration through Whatman 934-AH microfiber filters. The filtrate was subsequently concentrated 200-fold on a model DC2 hollow fiber dialyzer/concentrator unit equipped with HP2 (molecular weight cutoff of 2,000) hollow-fiber filters (Amicon Corp., Lexington, MA), dialyzed vs. water, and lyophilized.

Lyophilized acidified serum-free conditioned medium was dissolved in and dialyzed overnight vs. 100 mM sodium phosphate buffer, pH 6.6, filtered, and applied to a CM-cellulose column as described by Fett et al. (*Biochemistry* 24: 965–975, 1985). A typical experiment employed 6.3 mg of starting protein, from which 3.2 mg of fraction CM 1 (unbound), and 2.3 mg of fraction CM 2 (bound and eluted with 1M NaCl) were obtained. Both fractions were extensively dialyzed vs. water and lyophilized.

Purification of angiogenic material from the CM 2 fraction was achieved by reversed phase HPLC utilizing a Waters Associates liquid chromatography system consisting of a model 440 absorbance detector (254 nm), an LKB 2138 detector (206 nm), two model 6000 solvent delivery systems, a WISP 710A automatic sample loader, plus data module and systems controller. Fractionations were performed using an octadecylsilane Synchropak RP-P column (10 μm particle size, 250×4.1 mm) (Synchrom, Inc., Linden, IN) at a flow rate of 1 mL/min at room temperature. Column effluents were monitored at 206 nm and at 254 nm. Lyophilized preparations (CM 2) to be fractionated were reconstituted in 0.1% (v/v) trifluoroacetic acid (TFA) in water (Solvent A) (Mahoney & Hermodson, *J. Biol. Chem.* 255: 11199–111203, 1980) and applied to the column through the automatic sample injector. Columns were eluted with linear gradients using as final buffer isopropanol/acetonitrile/water (5:5:4 v/v/v) containing 0.08% TFA (Solvent C) over 120 min. Under these conditions, angiogenic activity eluted about 80 minutes after sample injection (~30% total organic concentration). Following elution, pooled fractions were dialyzed against water, lyophilized, and reconstituted for biological analyses. Chemical analyses were performed directly on column eluates.

Material from Pools C and D, (FIG. 1) which eluted at total organic concentrations of 29% and 30%, respectively, was electrophoresed on 15% SDS polyacrylamide gels essentially as described by Laemmli (*Nature* 227: 680–685, 1970) except that the stacking gel was omitted. Gels were silver stained using a commercially available kit (Bio-Rad Laboratories, Richmond, CA). Pool D was found to contain a single species with an apparent $M_r$ approximately 14,000. This species was designated as angiogenin. Pool C contained a major protein component of $M_r$ approximately 16,000 and lesser amounts of the $M_r$ approximately 14,000 species. The yield of angiogenin in Pool D was approximately 0.5 μg per L of conditioned medium.

Analogue dose-response analyses were performed on the two active fractions using the chick embryo CAM assay. Five μg of Pool C or D (plus 20 μg of lysozyme as carrier) were run on 15% gels as above. A control lane contained 20 μg of lysozyme alone. After electrophoresis the gel was washed twice for 15 min. each with 20% v/v isopropanol in PBS to remove SDS (Blank et al., *Anal. Biochem.* 120: 267–275, 1982) followed by three 10 min. washes with sterile water to remove the isopropanol. Gel slices (2.5 mm) were incubated for 72 hours in 200 μL of 5 mM sodium phosphate buffer, pH 7.0, containing 0.02% (w/v) BSA and supernatants were then assayed directly on the CAM for angiogenic activity. The efficiency of extraction for lysozyme, determined enzymatically, was 20%. Angiogenin (Pool D) was reproducibly active, $0.01\% \leq p \leq 5\%$ at levels ranging from 290 ng/egg to 0.5 ng/egg (i.e., from 20 pmol to 35 fmol/egg), the major change in response occurring below 1.4 ng/egg.

Pool C was also active but less so than Pool D. Thus, Pool C reached a significance level of $\leq 5\%$ only above 40 ng/egg. These data suggest that the angiogenic activity in Pool C may be due to the $M_r$ approximately 14,000 species detected in this region.

Angiogenin also induced the growth of new blood vessels when implanted in a pocket in the rabbit cornea. Considerable outgrowth of new vessels from the limbus toward and into the area of sample implantation can be seen. No vessel growth was observed in control experiments employing equivalent amounts of lysozyme. Positive angiogenic responses are observed reproducibly in the rabbit cornea at a level of approximately 50 ng (3.5 pmol).

CAM angiogenic activity at a significance level of $<0.2\%$ was eluted from gel slices from the region of the electropherogram corresponding to $M_r$ approximately 14,000 after 15% SDS-PAGE of an angiogenin/lysozyme mixture. No activity (significance level $>50\%$) was eluted from slices from an adjacent control lane containing lysozyme alone.

Angiogenin was also assayed for ribonuclease activity. Material purified as described above was subjected to an additional purification step on CM cellulose as described by Fett et al. (ibid). The bound fraction was eluted, lyophilized, and reconstituted in water. Aliquots of the reconstituted angiogenin were added to HT-29 cell RNA (isolated by the method of Chirgwin et al., *Biochemistry* 18: 5294, 1979) in 30 mM Tris pH 7.5 containing 30 mM NaCl. The mixture was incubated at 37° C. for 1 hour, and the reaction terminated by the addition of approximately 4 volumes of 26 mM MOPS, 6.5 mM sodium acetate, 1.3 mM EDTA, 65% formamide, 8% formaldehyde. Samples were analyzed by electrophoresis on a 1.1% agarose gel using the method of Lehrach et al. (*Biochemistry* 16: 4743, 1977). The RNA was visualized by ethidium bromide staining. Control samples, containing no angiogenin, contained two major RNA bands, corresponding to the 28S and 18S ribosomal RNAs. As increasing amounts of angiogenin were included, the levels of the 28S and 18S bands decreased, and increasing amounts of lower molecular weight material were observed. At least one new discrete band was incubated with angiogenin for extended periods. These results indicate that angiogenin is a ribonuclease capable of making only a small number of cuts (probably $<5$) in both the 28S and 18S ribosomal RNAs.

An isolate from cell line HT-29 has been deposited with American Type Culture Collection under accession number ATCC No. CRL8905.

Example 2: Chemical Characterization of Angiogenin

The molecular weight of angiogenin was estimated by both SDS-PAGE and gel-filtration HPLC in the presence of guanidine hydrochloride. Both yielded a $M_r$ of approximately 14,000. For amino acid and sequence analysis, proteins were reduced with tributylphosphine in 0.25M sodium bicarbonate in n-propanol (50% in water) and alkylated with 1,3-propane sultone (Sigma Chemical Co.) according to the method of Ruegg & Rudinger, (*Int. J. Pept. Prot. Res.* 6: 447–456, 1974). Alkylated samples were desalted by chromatography on an I-125 HPLC column (Waters Associates) in 17.9% (v/v) acentonitrile, 17.9% (v/v) isopropanol, 0.1% (v/v) TFA in water. Performic acid oxidation was done according to Moore, (*J. Biol. Chem.* 238: 235–237, 1963). Lyophilized samples were hydrolyzed in vacuo with 6N HCl and 0.1% phenol for 20 hours at 110° C. (Sanger & Thompson, *Biochim. Biophys. Acta* 71: 468–471, 1963). Hydrolysates were dried under vacuum at 25°–35° C., redissolved in citrate buffer, pH 2.2, and analyzed on a Durrum D-500 amino acid analyzer using ninhydrin as reagent. A Hewlett Packard 3390A integrator was used for quantitation.

Automated Edman degradation was performed on 300 to 3,000 pmol of protein with Beckman 890C sequencer using 0.1M quadrol coupling buffer with Beckman program 121078 as described (Fett et al., ibid). Carboxyl terminal determinations were performed on 200 pmol of protein by hydrazinolysis with anhydrous hydrazine (Pierce Chemical Co., Rockford, IL) for 18 hours at 80° C. in vacuo (Akabori et al., *Bull. Chem. Soc. Japan* 25: 214–218, 1952) followed by direct analysis of hydrolysates by the "Pico-Tag" method (Waters Associates; Bidlingmeyer et al., *J. Chromatography* 336: 93–104, 1984).

Six cycles of Edman degradation performed on either native or performic acid oxidized protein did not reveal a free end group. Only a single carboxyl terminal amino acid, proline, was found after hydrazinolysis. Furthermore, no lower molecular weight subunits were found when angiogenin was examined by SDS-polyacrylamide gel electrophoresis in the presence of 2-mercaptoethanol. Taken together, these data indicate that angiogenin is a single chain polypeptide. Amino acid analysis gave a $M_r$ value for angiogenin of approximately 14,400.

analytical isoelectric focusing (IEF) and cation-exchange HPLC demonstrated that angiogenin is extremely basic. It migrates to the front during IEF, indicating an isoelectric point greater than 9.5. Additionally, angiogenin elutes after lysozyme (pI=10.5) in cation-exchange HPLC. This behavior is consistent with its binding to CM-cellulose under the conditions employed and suggests that along with its high content of basic amino acids many of the side-chain carboxyl groups are amidated.

Isolation of Tryptic Peptides. Angiogenin in lots of 12–66 μg was digested with HPLC purified trypsin (Titani et al., *Anal. Biochem.* 123: 408–412, 1982), 2 to 3% by weight, in 100 μL of 0.1M N-ethylmorpholine buffer, pH 8.5, at 35° C. for 18–20 hours under $N_2$. The larger peptides from tryptic digests were then isolated by chromatography on an Altex Ultrapore C3 column (Beckman Instruments, Inc.). The breakthrough fraction was rechromatographed on an Altex Ultraphere-IP (Beckman Instruments, Inc.) column employing either a volatile (0.1% TFA) or a non-volatile (0.1M perchlorate-0.1% phosphate, pH 2.5) buffer (Meek, *Proc. Natl. Acad. Sci. USA* 77: 1632–1636, 1980). In the latter case, the peptides had to be desalted prior to sequencing by chromatography on an IBM 5-μm C18 column with 0.1% HFBA and acetonitrile as solvents. Peptide NT 1 was desalted by reversed-phase phase chromatography on a C18 column, using 0.1% TFA and acetonitrile as solvents. Peptides were analyzed for amino acid composition as described above.

Sequences of the Tryptic Peptides. Table 1 presents the sequences derived from Edman degradation of each of the peptides isolated as outlined above.

TABLE 1
Amino Acid Sequences of Tryptic Peptides of Angiogenin Obtained by Micro Edman Degradation

| Peptide | Sequencer Results[a] |
|---|---|
| NT 1 + 13 | Arg—Arg<br>163 108 |
| NT 2 | Arg—Pro<br>20 |
| NT 3a | Ser—Ile—Lys<br>890 795 163 |
| NT 3b | (Arg+Ile)—Ser—Lys<br>264 273 144 43 |
| NT 4a | Asn—Gly—Asn—Pro—His—Arg<br>103 168 80 139 ~50 ~20 |
| NT 4b | Ala—Ile—Cys—Glu—Asn—Lys<br>570 505 100 83 100 25 |
| NT 5 | Glu—Asn—Leu—Arg<br>500 270 1000 70 |
| NT 6 | Ala—Thr—Ala—Gly—Phe—Arg<br>640 258 471 252 136 32 |
| NT 7 | Tyr—Thr—His—Phe—Leu—Thr—Glu—His—Tyr—Asp—<br>314 340 100 235 268 167 170 17 156 30<br>Ala—Lys—Pro—Glu—Gly—Arg<br>228 86 44 42 54 trace |
| NT 8 | Asp—Ile—Asn—Thr—Phe—Ile—His—Gly—Asn—Lys<br>147 283 120 150 235 231 10 150 20 56 |
| NT 9 (NT 9' + 9") | (Asp+Ser)—(Asp+Ser)—(Arg+Phe)—(Gln+Tyr)—<br>403 465 458 571 151 290 232 285<br>Val—(Thr+Glu)—(Thr+Ser)—Ile—(Met+Lys)<br>660 205 256 120 172 133 236 13 |
| NT 10 (NT 10' + NT 10") | (Gly+Leu)—(His+Leu)—(Thr+Gly)—(Ser+Gly)—<br>862 909 171 745 323 861 405 833<br>(Ser+Pro)—Pro—(Trp+Lys)—Pro—Pro-Nothing-<br>455 255 460 206 12 437 382<br>Gln-Tyr<br>130 133 |
| NT 11 (NT 4b + NT 12) | (Asn+Ala)—(Val+Ile)—Val—(Val+Glu)—(Asn+Ala)—<br>25 250 253 140 212 200 70 10 202<br>nothing-Glu—Asn—Gly—Leu<br>7 trace 58 56 |
| NT 12 | Asn—Val—Val—Val—Ala—Cys—Glu—Asn—Gly—Leu—<br>467 756 756 562 683 150 105 70 118 204<br>Pro—Val—His—Leu—Asp—Gln—Ser—Ile—Phe—Arg<br>119 212 50 188 24 20 108 36 72 33 |

[a]The established sequence is given, with the yield of amino acid residue at each cycle given below the residue, in pmol. The parentheses indicate that two residues were found after a given degradation cycle.

Unique sequences were found for peptides NT 3a, NT 4a, NT 4b, NT 5, NT 6, NT 7, NT 8 and NT 12; consequently these were considered pure. Analysis of peptide NT (1+13) gave the sequence Arg—Arg. This, together with its composition, indicated that NT (1+13) was a mixture of Arg—Arg and the N-blocked amino terminal peptide, NT 1. Desalted peptide NT 1 was analyzed by FAB-mass spectrometry and found to have a MH+ of 602, indicating the presence of pyroglutamic acid, Asp, Asn, Ser and Arg. The symbol <Glu is employed in the drawing and in the claims to represent a pyroglutamic acid moiety. Peptide NT 2 gave Arg on the first degradation cycle, but nothing after that. It composition, Arg plus Pro, and the fact that the carboxyl terminal residue of angiogenin is Pro, identified the sequence of NT 2 as Arg—Pro and located it at the carboxyl terminus of angiogenin. Peptide NT 3b gave both Arg and Ile on the first cycle but only Ser and Lys thereafter. Hence, NT 3b is probably the tripeptide Ile—Ser—Lys plus free arginine. Both NT 9 and NT 10 were found to be mixtures of two peptides (designated NT 9' plus NT9" and NT 10' and NT10", respectively) probably linked by a disulfide bond in each instance. NT 11 is also a mixture. In this case, comparison of its sequence information with that of NT 4b and NT 12 demonstrated that NT 11 consisted of these two peptides linked by a disulfide bond.

Jointly, these peptides account for nearly the entire amino acid composition of angiogenin.

A thermolysin digest of 700 pmol of reduced and S-sulfopropylated angiogenin enabled the isolation of six pure peptides whose amino acid compositions were determined (Table 2). Three of these were helpful in providing overlaps for the tryptic peptides.

TABLE 2
Amino Acid Composition of Some Thermolysin Peptides of Angiogenin

| Peptide | L1 | L2 | L3 | L4 | L5 | L6 |
|---|---|---|---|---|---|---|
| Cys(Sp) |  | 0.43(1) |  |  |  |  |
| Asp[a] | 0.55(1) |  |  | 0.81(1) | 0.50(1) |  |
| Thr |  | 1.97(2) | 0.68(1) |  |  |  |
| Ser | 0.94(1) | 0.46 | 0.56 | 0.73(1) | 0.46 | 0.15 |
| Glu[a] | 0.80(1) | 0.58 | 0.92(1) | 0.37 | 0.30 |  |
| Pro |  |  |  |  |  |  |
| Gly | 0.38 | 0.48 | 0.71 | 1.39(1) | 0.63 | 0.31 |
| Ala |  |  |  |  |  | 0.71(1) |
| Val |  | 0.95(1) |  |  |  |  |
| Met |  |  |  |  |  |  |
| Ile |  |  |  | 0.68(1) |  | 1.00(1) |
| Leu | 1.17(1) |  | 1.03(1) |  |  | 0.16 |
| Tyr |  |  |  |  |  |  |
| Phe |  |  |  | 1.04(1) | 0.94(1) | 0.13 |
| His |  |  | 0.92(1) | 0.78(1) | 0.14 |  |
| Lys |  | 1.19(1) |  | 0.56(1) |  | 1.00(1) |
| Arg | 0.17 |  |  | 1.32(1) | 1.03(1) |  |
| Total | 4 | 5 | 4 | 8 | 3 | 3 |
| Sequence | 115–118 | 78–82 | 10–13 | 45–52 | 100–102 | 53–55 |

TABLE 2-continued
Amino Acid
Composition of Some Thermolysin Peptides of Angiogenin

| Peptide | L1 | L2 | L3 | L4 | L5 | L6 |
|---------|----|----|----|----|----|----|
| Position | | | | | | |

*Asp and Glu are low (by 30-50% and 5-20%, respectively) due to the presence of salt which interfered with the PITC-reaction.

Alignment of the Tryptic Peptides. Because Edman degradation indicates that the amino terminus of angiogenin is blocked and the mass spectrometric evidence indicates that NT 1 contains <Glu it appeared that this must be the N-terminal residue. Therefore, 140 µg of the intact protein was digested with pyroglutaminase in order to render the amino terminus accessible to Edman degradation. The product, isolated by reversed-phase HPLC, was then processed through 40 cycles of degradation. As expected, the amino terminus of the digested protein was no longer blocked. Thirty-five of the first 36 cycles were identified, providing the sequence of NT 1, aligning NT 7 as the next peptide and supplying the sequence of the NT 9' component of NT 9 and part of the sequence of the NT 10' component of NT 10 while aligning them into the amino terminal sequence. The rest of the sequence of NT 10' was determined from the analysis of NT 10. In addition, NT 10' was isolated by HPLC after reduction and alkylation of NT 10. It had the following composition: CysCM 0.46 (1), Glu 0.4, Ser 1.08 (1), Gly 1.39 (1), Arg 0.23, Thr 1.13 (1), Ala 0.23, Pro 1.27 (1), Leu 0.95 (1), Lys 0.80 (1), which is consistent with the assigned sequence. Peptide NT 13 and perhaps also the free Arg of NT 3b would fit into positions 32 and 33 of the overall sequence of angiogenin.

The amino terminal sequence demonstrate that the single methionine occupies position 30. Cyanogen bromide cleavage of the chain at that point allowed extension of its sequence for seven of the first eight residues following Met-30.

The overlap for peptides NT 3a and NT 4b in the order 3a-4b is provided by thermolysin peptide L 6 (Ile, Lys and Ala), which by thermolysin specificity (Feder & Schuck, *Biochemistry* 9: 2784-2791, 1970) must have the sequence Ile—Lys—Ala. Thermolysin specificity also dictates that the Ala of L 6 cannot be part of NT 6. This location of L 6 is also consistent with the sequence of peptide L 4 whose composition identifies it as extending from the Phe in peptide NT 8 through the Lys—Arg carboxyl terminus to the Ser of NT 3a. This therefore aligns peptides NT 8-3a-4b in that order.

The existence of two Asn—Gly sequences in angiogenin, in peptides NT 4a and NT 12 respectively, provided an opportunity for chemical cleavage of the polypeptide chain at these two positions by the hydroxylamine method of Bornstein (1970). The hydroxylamine digest was desalted by molecular sieve HPLC and the protein peak sequenced directly. A single clear sequence of 27 of 33 residues was obtained, enabling the alignment of peptides NT 4a-5-3b-9''-10'', in that order, and thereby placing an additional block of 35 residues in sequence. The salt-containing fraction of the hydroxylamine digest was refractionated by reversed-phase chromatography and one pure peptide, hydroxylamine-2, was isolated. Its amino acid composition was: Asp 1.17 (1), Glu 1.12 (1), Ser 0.99 (1); Gly 1.10 (1), His 0.84 (1), Arg 2.05 (2), Pro 2.11 (2), Tyr 0.22, Val 0.97 (1), Ile 0.81 (1), Leu 1.77 (2), and Phe 1.02 (1). These amino acids provide the overlap allowing alignment of NT 12 and NT 2, in that order.

Peptide L 5 (Phe, Arg, Asx) could arise from two different combinations of tryptic peptides—NT 8 or NT 12 providing its amino terminal Asx, and NT 6 providing its carboxyl terminal Phe—Arg sequence. The actual combination NT 6-12 was deduced on the basis of homology to the family of pancreatic ribonucleases as determined by a comparison of this region with the protein sequences in the National Biomedical Research Foundation protein sequence databank. The other three thermolysin peptides—L 1, L 2, and L 3—correspond to sequences identified within peptides NT 12, NT 9'', and NT 7.

Finally, the assignment of peptide NT 2 as the carboxyl terminal peptide is in agreement with the fact that proline is the carboxyl terminal amino acid residue of angiogenin.

Analysis of the amino acid sequence of angiogenin (shown in FIG. 2) indicated that the protein has a molecular weight of 14,193 daltons.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A substantially pure human protein having the amino acid sequence:

```
   1
<Glu—Asp—Asn—Ser—Arg—Tyr—Thr—His—Phe—Leu—
              15
Thr—Gln—His—Tyr—Asp—Ala—Lys—Pro—Gln—Gly—
                                      30
Arg—Asp—Asp—Arg—Tyr—Cys—Glu—Ser—Ile—Met—

Arg—Arg—Arg—Gly—Leu—Thr—Ser—Pro—Cys—Lys—
                 45
Asp—Ile—Asn—Thr—Phe—Ile—His—Gly—Asn—Lys—
                                      60
Arg—Ser—Ile—Lys—Ala—Ile—Cys—Glu—Asn—Lys—

Asn—Gly—Asn—Pro—His—Arg—Glu—Asn—Leu—Arg—
                 75
Ile—Ser—Lys—Ser—Ser—Phe—Gln—Val—Thr—Thr—
                                      90
Cys—Lys—Leu—His—Gly—Gly—Ser—Pro—Trp—Pro—

Pro—Cys—Gln—Tyr—Arg—Ala—Thr—Ala—Gly—Phe—
                105
Arg—Asn—Val—Val—Val—Ala—Cys—Glu—Asn—Gly—
                                     120
Leu—Pro—Val—His—Leu—Asp—Gln—Ser—Ile—Phe—

123
                            Arg—Arg—Pro—OH.
``` said protein characterized in that about 50 ng of the protein produces a positive angiogenic response in the rabbit cornea implantation test.

2. A therapeutic composition comprising a therapeutically effective amount of protein according to claim 1 and a pharmaceutically effective carrier.

* * * * *